United States Patent [19]

Balani et al.

[11] Patent Number: 5,387,512
[45] Date of Patent: Feb. 7, 1995

[54] PREPARATION OF 3-[Z-BENZOXAZOL-2-YL)ETHYL]-5-(1-HYDROXYETHYL)-6-METHYL-2-(1H)-PYRIDINONE BY BIOTRANSFORMATION

[75] Inventors: Suresh K. Balani, Hatfield; Steven M. Pitzenberger, Lansdale; Harri G. Ramjit, Lansdale, all of Pa.

[73] Assignee: Merck & Co. Inc., Rahway, N.J.

[21] Appl. No.: 841,240

[22] Filed: Feb. 24, 1992

Related U.S. Application Data

[63] Continuation of Ser. No. 712,317, Jun. 7, 1991, abandoned.

[51] Int. Cl.$^6$ ............................................. C12P 17/16
[52] U.S. Cl. ..................................................... 435/118
[58] Field of Search ......................................... 435/118

[56]     References Cited
PUBLICATIONS

Ratner, L. et al., "Complete nucleotide sequence of the AIDS virus, HTLV-III," Nature 313, 277 (1985).
Toh, H. et al., "Close structural resemblance . . . , " EMBO Journal 4, 1267 (1985).
Power, M. D. et al., "Nucleotide Sequence of SRV-1," Science 231, 1567 (1986).
Pearl, L. H. et al., "A Structural Model for Retroviral Proteases," Nature 329:351 (1987).
Paine, J. B., "A Convenient Synthesis of Nicrotinate Esters . . . ," J. Heterocyclic Chem. 24, 351 (1987).
Azri, S. et al., "Precision-Cut Liver Slices," In Vitro Toxicology 3, 309 (1990).
Smith, P. F. et al., "Dynamic Organ Culture of Precision Liver Slices for In Vitro Technology", Life Sciences 36:1367–75 (1985).
Krumdieck, C. L. et al., "A New Instrument for Rapid Preparation of Tissue Slices," Anal. Biochem. 104, 118 (1980).
Chapman, D. E. et al., "Metabolism and Covalent Binding of 14-toluene by Human and Rat Liver Microsomal Fractions," Drug Metabolism and Disposition 18, 929 (1990).
Goldman, M. E. et al., "Pyridinone derivatives: Specific HIV-1 reverse transcriptase inhibitors with antiviral activity," Proc. Nat. Acad. Sci. 88, 6863 (1991).

*Primary Examiner*—Douglas W. Robinson
*Assistant Examiner*—S. Saucier
*Attorney, Agent, or Firm*—Roy D. Meredith; Charles M. Caruso

[57]     ABSTRACT

Incubation of

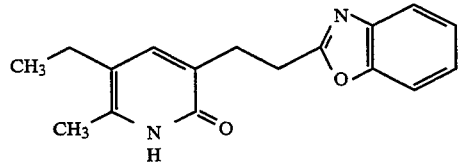

with a preparation from mammalian organ yields as biotransformation product the compound 3-[2-(benzoxazol-2-yl)ethyl]-5-(1-hydroxyethyl)-6-methyl-2-(1H)-pyridinone. This product is useful in the prevention or treatment of infection by HIV and the treatment of AIDS.

1 Claim, No Drawings

PREPARATION OF 3-[Z-BENZOXAZOL-2-YL)ETHYL]-5-(1-HYDROXYETHYL)-6-METHYL-2-(1H)-PYRIDINONE BY BIOTRANSFORMATION

This is a continuation of application Ser. No. 712,317, filed Jun. 7, 1991 abandoned.

The present invention relates to a novel process for the preparation of compound (I)

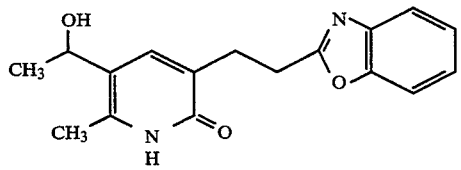

comprising incubation of compound (II), an inhibitor of the reverse transcriptase encoded by human immunodeficiency virus (HIV),

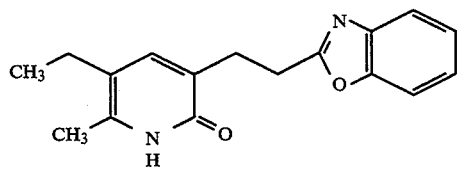

with a preparation from mammalian organ. Compound (I) or the pharmaceutically acceptable esters thereof inhibit the reverse transcriptase encoded by HIV and are of value in the prevention of infection by HIV, the treatment of infection by HIV and the treatment of the resulting acquired immune deficiency syndrome (AIDS).

The present invention is concerned with a compound which inhibits the reverse transcriptase encoded by human immunodeficiency virus (HIV) or pharmaceutically acceptable ester thereof and is of value in the prevention of infection by HIV, the treatment of infection by HIV and the treatment of the resulting acquired immune deficiency syndrome (AIDS).

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a vitally encoded reverse transcriptase to generate DNA copies of HIV sequences, a required step in vital replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compound prepared by the process of this invention is an inhibitor of HIV reverse transcriptase. Since the compound itself is a metabolite, it is better adapted as a pharmaceutical product. Further, the compound of the present invention does not require bio-activation to be effective.

BRIEF DESCRIPTION OF THE INVENTION

The novel process of this invention comprises incubation of Compound II

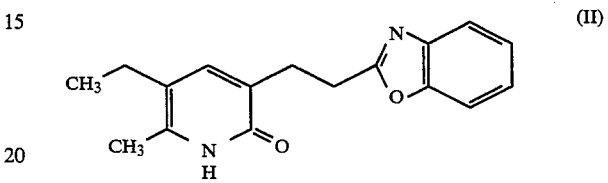

with a preparation from a mammalian organ, and isolation of the resulting biotransformation product, Compound (I), in a conventional manner.

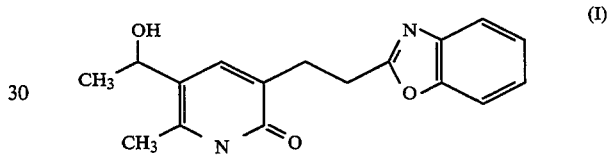

This compound is useful in the inhibition of HIV reverse transcriptase, the prevention of infection by HIV, the treatment of infection by HIV and in the treatment of AIDS and/or ARC, either as a compound, pharmaceutically acceptable salt (when appropriate), hydrate, ester, pharmaceutical composition ingredient, whether or not in combination with other antivirals, anti-infectives, immunomodulators, antibiotics or vaccines.

DETAILED DESCRIPTION OF THE INVENTION AND PREFERRED EMBODIMENTS

The novel process of this invention comprises incubation of compound (II)

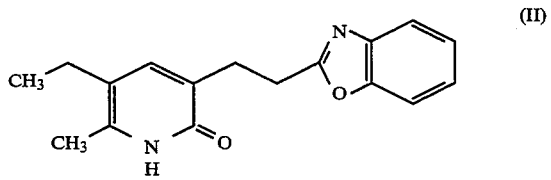

with a preparation from mammalian organ, and isolation of the resulting biotransformation product, compound (I), in a conventional manner.

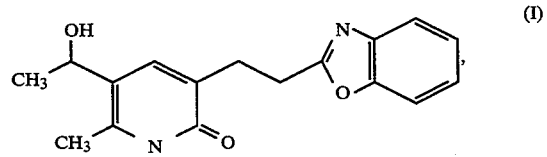

3-[2-(benzoxazol-2-yl)ethyl]-5-(1-hydroxyethyl)-6-methyl-2(1H)-pyridinone.

In general, compound (I), which is a 5-(1-hydroxy)-ethyl oxidation product, can be produced by incubating an appropriate amount of substrate compound (II) with certain mammalian tissues or cell cultures in an aqueous medium suitable for enhancing the viability of the tissues or cells. Metabolite (I) may be produced by incubation of compound (II) with a preparation from mammalian organ containing: a) preparations from surgically derived specimens including liver, kidneys, lungs and skin, both from animals and human beings; b) prenatal and gestational tissues; c) cell cultures; d) subcellular fractions like microsomes, S9 and cytosol; and/or e) purified mixed function oxidases or flavin monooxygenases. These metabolites could also be formed in vivo in animals and human beings. The preferred tissue for production of compound (I) is liver, especially rat liver slices.

The appropriate amount of tissue or cell culture to be used with a given amount of substrate compound will vary with the particular type of culture used. An appropriate ratio of substrate compound (II) to be incubated with liver tissue (mg:g, wet weight) ranges from about 1:0.3 to 1:3.0, preferably 1:2.4. When using surgically derived specimens, especially liver, the specimen is preferably cut into slices with thickness ranging from about 100µ to 1000µ, and more preferably from about 250 to 400µ.

Aqueous media sufficient in amount and kind to keep the tissue or cells healthy in the incubation process should be used. These media are known and available in the art of drug metabolism and include various buffers and standard culture media with or without additives. A few examples of various culture media that may be employed are Williams' Medium E, Waymouth's Medium, Dulbecco's Medium, RPMI Medium and the like. Culture media could be replaced by general buffers such as phosphate buffers. Various additives that may be used to enhance the viable life of the cells and tissues are a) serum from bovine, horse, chicken, goat, sheep, rabbit and the like; b) HEPES or MOPS; c) gentamycin; and d) insulin, for example. A preferred medium for incubation of substrate compound (II) with rat liver slices is Williams' Medium E.

The material is incubated at a temperature between 35° and 39° C., preferably 37° C., and at a pH between 7.2 and 7.6, preferably 7.4, under an atmosphere of 0% to 5% carbon dioxide in oxygen, or 100% air. The material is incubated for a period of time necessary to complete the oxidative biotransformation as monitored by HPLC (high perfomance liquid chromatography), usually for a period of about four hours when incubated with rat liver slices.

The biotransformation product (I) can be isolated and purified from the incubation mixture by extraction with a conventional solvent, such as methylene chloride, ethyl acetate, acetonitrile, methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using ethyl acetate. A preferred purification method involves the use of chromatography, especially HPLC, using a bonded silica gel column. Eluant mixtures for chromatography can be composed of water and an organic solvent such as methanol, acetonitrile and the like, and may optionally include a small amount of base, such as ammonium bicarbonate, or an acid, such as trifluroacetic acid or phosphoric acid. A preferred eluant is composed of acetonitrile and water containing 0.1% ammonium bicarbonate and is run through the column with a linear gradient.

A process for making esters of (I) is also encompassed by the present invention. Such esters are those which would readily occur to the skilled artisan, and include, for example, $C_{1-4}$ alkyl esters. The biotransformed compound of this invention has an asymmetric center and may occur as a racemate, racemic mixture, mixture of enantiomers, or as an individual enantiomer, with all enantiomeric forms being included in the present invention.

The compound of the present inventions is useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compound of this invention is useful in treating infection by HIV after suspected past exposure to HIV by, e.g., blood transfusion, organ transplant, exchange of bodily fluids, bites, accidental needle stick, or exposure to patient blood during surgery.

EXAMPLE 1

3-[2-(Benzoxazol-2-yl)ethyl]-5-ethyl-6-methyl-2-(1H)-pyridinone, substrate compound (II)

Step. A: Preparation of 3-cyano-5-ethyl-6-methyl-2-(1H)-pyridinone

According to the method described in J. Heterocyclic Chem., 24, 351 (1987), a mixture of 2-ethyl-3-oxobutanal, sodium salt (37.5 g, 0.275 mmol), cyanoacetamide (25.2 g, 0.30 mol), aqueous piperidinium acetate (22 mL) [prepared from glacial acetic acid (4.2 mL), water (10 mL) and piperidine (7.2 mL)] in water (775 ml) was refluxed for four hours. Glacial acetic acid (30 ml) was added cautiously (much foaming) as the product precipitated. Upon cooling to room temperature, the product was collected by filtration, washed with cold water and air dried to yield 22.3 g (50%), m.p. 237°–240° C.

step B: Preparation of 5-ethyl-6-methyl-2-(1H)-pyridinone-3-carboxylic acid

An initial suspension of 5-ethyl-6-methyl-2-(1H)-pyridinone (4.86 g, 30 mmol) in 6N HCl (100 mL) was heated at reflux for twenty hours. Upon cooling, the product crystallized and was collected by filtration, washed with cold water and air dried to yield 3.73 g (69%).

Step C: Preparation of methyl 2-chloro-5-ethyl-6-methyl nicotinate

A mixture of 5-ethyl-6-methyl-2-(1H)-pyridinone-3-carboxylic acid (3.62 g, 20 mmol) and phosphorus pentachloride (4.38 g, 21 mmol) was heated, under a nitrogen atmosphere, at 100°–120° C. for 1.5 hours. The cooled residue was diluted with chloroform (70 mL) and then methanol (15 mL) was added. After stirring for 2–16 hours, the solution was poured into ice/water. The organic layer was separated and washed successively with water, saturated aqueous NaHCO₃, dried (Na₂SO₄), filtered and the solvent evaporated. This dark amber oil was dissolved in hexane, filtered through a pad of charcoal and the solvent evaporated to yield 3.31 g (78%) of pure product as a light yellow oil.

Step D: Preparation of methyl 2-methoxy-5-ethyl-6-methylnicotinate

To a solution of sodium metal (0.55 g, 24 mmol) dissolved in anhydrous methanol (15 mL), under a nitrogen atmosphere, was added a solution of methyl 2-chloro-5-ethyl-6-methylnicotinate (3.18 g, 14.9 mmol) in dry methanol (5 mL). This solution was refluxed and monitored by tlc (thin layer chromatogram) until the starting material had been consumed (about 24 hours). The cooled mixture was diluted with diethyl ether (50 mL), washed with water, saturated aqueous NaHCO₃, dried (Na₂SO₄), filtered and the solvent evaporated to yield 2.28 g (73%) of pure product as a light yellow oil.

Step E: Preparation of 2-methoxy-3-hydroxymethyl-5-ethyl-6-methyl pyridine

To a solution of methyl 2-methoxy-5-ethyl-6-methylnicotinate (2.28 g, 10.9 mmol) in anhydrous tetrahydrofuran (50 mL), under a nitrogen atmosphere, was added cautiously lithium aluminum hydride (0.77 g, 20 mmol). After refluxing this mixture for 15-20 hours, saturated aqueous Na₂SO₄ was added carefully to quench the cooled reaction mixture. This mixture was diluted with more THF, dried (Na₂SO₄), filtered and the solvent evaporated. This residue was chased with ethanol/toluene to remove traces of water and triturated with hexane as the product slowly crystallized out to give 1.30 g (66%), mp 53°-55° C.

Step F: Preparation of 2-methoxy-5-ethyl-6-methyl nicotinaldehyde

Activated manganese dioxide (2.0 g) was added to a solution of 2-methoxy-3-hydroxymethyl-5-ethyl-6-methylpyridine (1.18 g, 6.5 mmol) in dry benzene (20 mL) and refluxed 5-10 hours. The warm suspension was filtered through a pad of anhydrous Na₂SO₄ and evaporated to yield 1.05 g (90%) of a viscous oil which solidified.

Step G: Preparation of 2-[2(R/S)-hydroxy-2-(2-methoxy-5-ethyl-6-methyl-pyridin-3-yl)ethyl]benzoxazole.

To a solution of 2-methylbenzoxazole (226 mg, 1.7 mmol) in anhydrous THF (4 mL), cooled to −100° C. under an argon atmosphere, was added 1.6M n-butyllithium/hexane (1.05 mL) slowly over 35 minutes. After 0.5 hour a solution of 2-methoxy-5-ethyl-6-methylnicotinaldehyde (300 mg, 1.7 mmol) in dry THF (1 mL) was added dropwise. The reaction was allowed to warm to room temperature and poured onto crushed ice. This mixture was extracted with diethyl ether. The combined extracts were dried (MgSO₄) and the solvent removed to give an oil which was flash chromatographed over silica gel. Elution with ethyl acetate/hexane (1:19) gave 340 mg (65%) of analytically pure racemic product, mp 102°-103° C.

Anal. Calcd for $C_{18}H_{20}N_2O_3 \cdot 0.1 H_2O$: C, 68.81; H, 6.48; N, 8.92. Found: C, 68.80; H, 6.76; N, 8.95.

Step H: Preparation of 3-[2-(benzoxazol-2-yl)-ethenyl]-5-ethyl-6-methyl-2-(1H)-pyridinone A mixture of 2-[2(R/S)-hydroxy-2-(2-methoxy-5-ethyl-6-methylpyridin-3-yl)ethyl]benzoxazole (72 mg, 0.23 mmol) and pyridine hydrochloride (133 mg, 1.2 mmol), under a nitrogen atmosphere, was placed in a preheated oil bath (165° C.) for 5 minutes. The reaction flask was removed, cooled, and water added to give a solid. This crude product was extracted into chloroform, dried (MgSO₄) and the solvent evaporated to yield 49 mg (75%) of pure product. Recrystallization from methanol gave 15 mg of analytically pure product, mp 262°-264° C.

Anal. Calcd for $C_{17}H_{16}N_2O_2$: C, 72.83; H, 5.75; N, 10.00. Found: C, 72.93; H, 5.95; N, 9.99.

Step I: Preparation of 3-[2-(benzoxazol-2-yl)ethyl]-5-ethyl-6-methyl-2-(1H)-pyridinone A solution of 80% pure 3-[2-(benzoxazol-2-yl)ethenyl]-5-ethyl-6-methyl-2-(1H)-pyridinone (200 mg) in methanol/ethanol/THF (25 mL, 1:1:1) was hydrogenated at atmospheric pressure over 5% palladium/charcoal for four hours. After filtering off the catalyst, the solvents were evaporated and the residue flash chromatographed over silica gel. Elution with 2% methanol-98% chloroform gave 75 mg of analytically pure product, mp 155°-156.5° C.

Anal. Calcd. for $C_{17}H_{18}N_2O_2$ C, 72.31; H, 6.43; N, 9.92. Found: C, 72.45; H, 6.52; N, 9.99.

EXAMPLE 2

Another, simpler procedure for the synthesis of the product of Example 1 is as follows.

Step A: Preparation of 3-cyano-5-ethyl-6-methyl-2-(1H)-pyridinone

Accordingly to the method described in J. Heterocyclic Chem., 24, 351 (1987), a mixture 2-ethyl-3-oxobutanol, sodium salt (37.5 g, 0.275 mol), cyanoacetamide (25.2 g, 0.30 mol), aqueous piperidinium acetate (22 mL) [prepared from glacial acetic acid (4.2 mL), water (10 mL) and piperidine (7.2 mL)] in water (775 ml) was refluxed for four hours. Glacial acetic acid (30 ml) was added cautiously (much foaming) as the product precipitated. Upon cooling to room temperature, the product was collected by filtration, washed with cold water and air dried to yield 22.3 g (50%), m.p. 237°-240° C.

New

Step B: Preparation of 2-chloro-3-cyano-5-ethyl-6-methylpyridine

3-Cyano-5-ethyl-6-methyl-2-(1H)-pyridinone (22.9 g, 0.141 mol) and phosphorus pentachloride (33.1 g, 0.159 mol) were intimately mixed and heated at 110°-120° C. for one hour. The liquified solids were poured onto crushed ice and water and the semi-solid was extracted into chloroform. This extract was washed with water, saturated aqueous NaHCO₃, dried (Na₂SO₄), filtered and evaporated. This amber oil was dissolved in hexane and the insoluble material was removed when filtered through a pad of charcoal. Removal of the solvent gave a light yellow oil which solidified (17.7 g). Trituration of this solid with cold hexane yielded 15.6 g (61%) of pure product, m.p. 63°-64° C.

New

Step C: Preparation of 2-methoxy-3-cyano-5-ethyl-6-methylpyridine

Sodium metal (3.25 g, 0.141 mol) was dissolved in dry methanol (100 mL) under a nitrogen atmosphere. When solution was complete, a slurry of 2-chloro-5-ethyl-6-methylpyridine (17.95 g, 99.4 mmol) in dry methanol (70 mL) was added and the reaction was warmed at 60° C. for 15-20 hours. After cooling the reaction mixture, diethyl ether (250 mL) and water (200 mL) were added. The ether layer was separated and washed with water, dried (Na₂SO₄), filtered and evaporated to give a light yellow solid (17.5 g). This solid was triturated with cold hexane to yield 14.4 g (82%) of pure product, m.p. 59°–61° C.
New
Step D: Preparation of 2-methoxy-5-ethyl-6-methyl-nicotinaldehyde To a solution of 2-methoxy-3-cyano-5-ethyl-6-methylpyridine (1.0 g, 5.68 mmol) in dry tetrahydrofuran (50 mL) under a nitrogen atmosphere and cooled to −70° C., was added 1.3$\underline{M}$ diisobutyl aluminum hydride/THF (17.4 mL, 22.7 mmol). The resulting mixture was allowed to warm to room temperature and stir for 15–20 hours. The reaction mixture was acidified with 1$\underline{N}$ hydrochloric acid and then neutralized with aqueous sodium bicarbonate. Water was then added and the product extracted into diethyl ether. The ethereal extract was dried ($Na_2SO_4$), filtered and the solvent evaporated. This residue was flash chromatographed on silica gel eluting with 10% diethyl ether/pentane to give 610 mg (61%) of product.

Step E (old step G): Preparation of 2-[2(R/S)-hydroxy-2-(2-methoxy-5-ethyl-6-methylpyridin-3-yl)ethyl]-benzoxazole To a solution of 2-methylbenzoxazole (226 mg, 1.7 mmol) in anhydrous THF (4 mL), cooled to −100° C. under an argon atmosphere, was added 1.6$\underline{M}$ n-butyllithium/hexane (1.05 mL) slowly over 35 minutes. After 0.5 hour a solution of 2-methoxy-5-ethyl-6-methyl-nicotinaldehyde (300 mg, 1.7 mmol) in dry THF (1 mL) was added dropwise. The reaction was allowed to warm to room temperature and poured onto crushed ice. This mixture was extracted with diethyl ether. The combined extracts were dried ($MgSO_4$) and the solvent removed to give an oil which was flash chromatographed over silica gel. Elution with ethyl acetate/hexane (1:19) gave 340 mg (65%) of analytically pure racemic product, mp 102°–103° C.

Anal. Calcd for $C_{18}H_{20}N_2O_3 \cdot 0.1\ H_2O$: C, 68.81; H, 6.48; N, 8.92. Found: C, 68.80; H, 6.76; N, 8.95.

Step F (old step H): Preparation of 3-[2-(benzoxazol-2-yl)-ethenyl]-5-ethyl-6-methyl-2-(1H)-pyridinone A mixture of 2-[2(R/S)-hydroxy-2-(2-methoxy-5-ethyl-6-methylpyridin-3-yl)ethyl]benzoxazole (72 mg, 0.23 mmol) and pyridine hydrochloride (133 mg, 1.2 mmol), under a nitrogen atmosphere, was placed in a preheated oil bath (165° C.) for 5 minutes. The reaction flask was removed, cooled, and water added to give a solid. This crude product was extracted into chloroform, dried ($MgSO_4$) and the solvent evaporated to yield 49 mg (75%) of pure product. Recrystallization from methanol gave 15 mg of analytically pure product, mp 262°–264° C.

Anal. Calcd for $C_{17}H_{16}N_2O_2$: C, 72.83; H, 5.75; N, 10.00. Found: C, 72.93; H, 5.95; N, 9.99.

Step G (old step I): Preparation of 3-[2-(benzoxazol-2-yl)ethyl]-5-ethyl-6-methyl-2-(1H)-pyridinone A solution of 80% pure 3-[2-(benzoxazol-2-yl)ethenyl]-5-ethyl-6-methyl-2-(1H)-pyridinone (200 mg) in methanol/ethanol/THF (25 mL, 1:1:1) was hydrogenated at atmospheric pressure over 5% palladium/charcoal for four hours. After filtering off the catalyst, the solvents were evaporated and the residue flash chromatographed over silica gel. Elution with 2% methanol-98% chloroform gave 75 mg of analytically pure product, mp 155°–156.5° C.

Anal. Calcd. for $C_{17}H_{18}N_2O_2$ C, 72.31; H, 6.43; N, 9.92. Found: C, 72.45; H, 6.52; N, 9.99.

EXAMPLE 3

Incubation With Rat Liver Slices.

Incubation of tritiated 3-[2-(benzoxazol-2-yl)ethyl]-5-ethyl-6-methyl-2-(1H)-pyridinone (parent compound/14.18 µmol) with rat liver slices (6.1 g) in 100 ml of Williams Medium E at pH. 7.4 and at 37° C. under a partial atmosphere of 95% $O_2$+5% $CO_2$ resulted in ~32% metabolism in four hours. Ethyl acetate extraction gave a recovery of ~70% of the tritiated material, while ~25% (~9 HPLC peaks) remained in the aqueous residue. Analysis of the aqueous residue showed that the unreacted parent compound was quantitatively extracted in ethyl acetate. HPLC of the organic extract on a µBondapak $C_{18}$ (7.8×300 mm) column eluted with 0.1% TFA containing $MeCN-H_2O$ gradient showed three significant radioactive peaks: M1 (~37% of the total metabolites), M2 (15%) and M3 (6%). The peaks M1 and M3 had UV spectra similar to the parent compound ($\lambda_{max}$ ~233, 270, 276, 313 nm), while M2 was lacking the UV band around 313 nm, suggesting a disruption in the pyridone conjugation system of M2. Notably, M1 and M2 co-eluted under analytical conditions using a (3.9×300 mm) $C_{18}$ column.

The major metabolite, M1, was separated on the prep HPLC column using a 0.1% TFA based acetonitrile-water gradient, then repurified using a methanol-water gradient.

EXAMPLE 4

Structural Determination: NMR

The structure of the M1 liver-slice metabolite of the parent compound was determined by NMR spectroscopy ($CD_3$, CN, 500 MHz) to be the hydroxylated derivative shown below. Key assignments of the benzoxazole ring protons were achieved by correspondence with the spectrum of 2-methylbenzoxazole (Aldrich; see below for full assignment by carbon and proton NMR studies). The 7- and 8-position methylenes were differentiated by irradiating H-4 in a difference NOE experiment and observing enhancements in H-9 and the 7-methylene at 2.9 ppm.

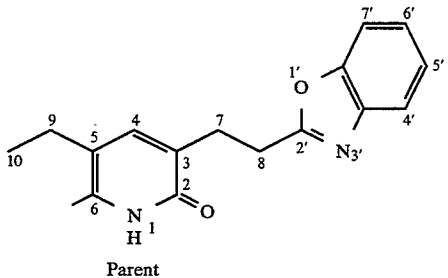

Parent

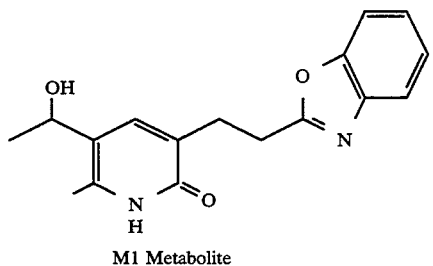

M1 Metabolite

| proton(s) | Parent | M1 Metabolite |
|---|---|---|
| 1 | 9.40(br s; 1H) | 9.40(br s; 1H) |
| 4 | 7.13(s; 1H) | 7.38(s; 1H) |
| 7 | 2.93(t; 7.4Hz; 2H) | 2.96(m; 2H) |
| 8 | 3.18(t; 7.4Hz; 2H) | 3.19(m; 2H) |
| 9 | 2.27(q; 7.6Hz; 2H) | 4.72(d of q; 3.6, 6.3Hz; 1H) |
| 10 | 0.94(t; 7.5Hz; 3H) | 1.15(d; 6.3Hz; 3H) |
| 11 | 2.14(s; 3H) | 2.17(s; 3H) |
| 9-OH | — | 2.90(d; 3.6Hz; 1H) |
| 4' | 7.62(m; 1H) | 7.62(m; 1H) |
| 5', 6' | ~7.31(m; 2H) | ~7.31(m; 2H) |
| 7' | 7.54(m; 1H) | 7.54(m; 1H) |

2-Methylbenzoxazole: (ca. 100 mg/ml in $CD_3CN$; 500 MHz; assignments via short and long-range HETCOR experiments)

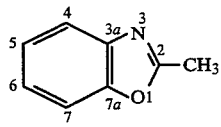

| position | proton δ (ppm) | carbon δ (ppm) |
|---|---|---|
| 2 | — | 165.1 |
| 2-$CH_3$ | 2.51 | 14.5 |
| 3a | — | 142.7 |
| 4 | 7.61 | 120.1 |
| 5 | ~7.30 | 125.0 |
| 6 | ~7.30 | 125.3 |
| 7 | 7.52 | 111.1 |
| 7a | — | 151.9 |

EXAMPLE 5

Structural Determination: FAB/MS

The fraction containing M1 was further subjected to Low Resolution and High Resolution FAB/MS analysis using a glycerol matrix. Comparative analyses were also performed on authentic parent compound.
Results Obtained Are As Follows:

| | Parent (M + H)⁺ | M1 (M + H)⁺ |
|---|---|---|
| Molecular ion | 283 | 299 |
| Measured mass | 283.144455 | 299.1384280 |

-continued

| | Parent (M + H)⁺ | M1 (M + H)⁺ |
|---|---|---|
| Empirical formula | $C_{17}H_{19}N_2O_2$ | $C_{17}H_{19}N_2O_3$ |
| Theoretical mass | 283.144653 | 299.139567 |

The observed molecular ion (M+H) at m/z 299.1384280 computes to an empirical formula of $C_{17}H_{19}N_2O_3$, which is consistent for the hydroxy analog of the parent compound.

EXAMPLE 6

Reverse Transcriptase Assay

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C).oligo d(G)$_{12-18}$. The inhibitor of the present invention inhibits this incorporation.

Thirty uL of a reaction mixture containing equal volumes of: 500 mM Tris.HCl (pH 8.2), 300 mM $MgCl_2$, 1200 mM KCl, 10 mM DTT, 400 μg/mL poly r(c).oligo d(G) [prepared by dissolving 1.5 mg (25 U) poly r(C).oligo d(G) in 1.5 ml sterile distilled $H_2O$ and diluting to 400 μg/ml], 0.1 μCi/μl [$^3$H] dGTP, 160 μM dGTP, was added to 10 μl sterile distilled $H_2O$, and 2.5 μl of potential inhibitor. An aliquot of 10 μL of 5 nM purified HIV $RT_R$ was added to initiate the reaction. The mixture was incubated at 37° C. for 45 minutes.

After incubation is complete, the tubes were cooled in ice for 5 minutes. Ice-cold 13% TCA containing 10 mM NaPP$_i$ (200 μl) are added and the mixture incubated on ice for 30 minutes. The precipitated cDNA is removed by filtration using presoaked glass filters [TCA, NaPP$_i$]. The precipitate is then washed with 1N HCl, 10 mM NaPP$_i$.

The filter discs are then counted in a scintillation counter.

Under these conditions [dGTP] and poly r(C).oligo d(G)$_{12-18}$ each are approximately equal to the appropriate Km value. Approximately 5–6,000 cpm of [$^3$H] GMP are incorporated into acid-precipitable material. The RT reaction is concentration- and time-dependent. DMSO (up to 5%) does not affect enzyme activity. The calculated IC$_{50}$ value for the compound (I) of this invention is about 710 nM.

EXAMPLE 7

Organic Synthesis of M1, The Compound of the Present Invention

Method I:

Example 1 is repeated, except that 2-ethyl-3-oxobutanal is substituted with 2-(1-benzyloxy)ethyl-3-oxobutanal. The benzyloxy protecting group is removed in a final step of hydrogenation over palladium on carbon, yielding product.

Method II:

Example 2 is repeated, except that 2-ethyl-3-oxobutanal is substituted with 2-(1-benzyloxy)ethyl-3-oxobutanal. The benzyloxy protecting group is removed in a final step of hydrogenation over palladium on carbon, yielding product.

While the foregoing specification teaches the principles of the present invention, with examples provided for the purpose of illustration, it will be understood that the practice of the invention emcompasses all of the usual variations, adaptations, or modifications, as come

What is claimed is:
1. A method of preparing the compound
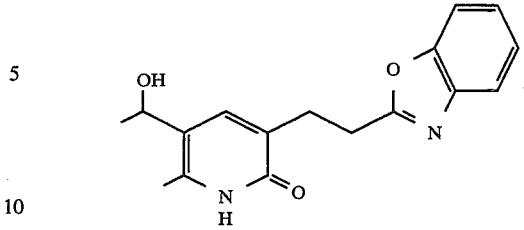
or ester thereof, comprising the steps of
(1) providing a quantity of 3-[2-(benzoxazol-2-yl)ethyl]-5-ethyl-6-methyl-2-(1H)-pyridinone,
(2) incubating the compound of step 1 with rat liver slices, and
(3) isolating the compound.